United States Patent [19]

Babb et al.

[11] Patent Number: 4,812,409

[45] Date of Patent: Mar. 14, 1989

[54] HYDROLYZABLE FLUORESCENT SUBSTRATES AND ANALYTICAL DETERMINATIONS USING SAME

[75] Inventors: Bruce E. Babb, Rochester; Robert T. Belly, Webster; Patricia M. Scensny, Rochester, all of N.Y.

[73] Assignee: Eastman Kodak Company, Rochester, N.Y.

[21] Appl. No.: 824,756

[22] Filed: Jan. 31, 1986

[51] Int. Cl.$^4$ .............................................. G01N 33/53
[52] U.S. Cl. .............................................. 435/7; 435/4; 435/18; 435/19; 435/23; 435/24; 435/29; 435/34; 435/38; 436/800; 530/322; 530/329; 530/330; 530/331; 536/1.1; 562/553; 562/516; 568/326
[58] Field of Search ............... 435/7, 18, 29, 38, 4; 568/326; 536/1.1; 530/322; 436/800; 260/502.5 R; 558/210

[56] References Cited

U.S. PATENT DOCUMENTS

| | | | |
|---|---|---|---|
| 4,144,306 | 3/1979 | Figuiras | 422/56 |
| 4,294,923 | 10/1981 | Smith et al. | 435/23 |
| 4,297,273 | 10/1981 | Buckler et al. | 436/800 |
| 4,404,366 | 9/1983 | Baguslaski et al. | 536/18.1 |
| 4,409,140 | 10/1983 | Smith et al. | |

FOREIGN PATENT DOCUMENTS

| | | |
|---|---|---|
| 122148 | 10/1984 | European Pat. Off. |
| 2031949 | 4/1980 | United Kingdom. |
| 80 02433 | 11/1980 | World Int. Prop. O. |

OTHER PUBLICATIONS

Feng et al, *Appl. Env. Microbiol.*, 43(6), pp. 1320–1329 (1982).
Wasilauskas et al, *J. Clin. Microbiol.*, 20(6) pp. 1205–1206 (1984).
Latt et al, *Cytometry*, 5, pp. 339–347 (1984).

*Primary Examiner*—Sam Rosen
*Attorney, Agent, or Firm*—J. Lanny Tucker

[57] ABSTRACT

Hydrolyzable substrates comprise blocked dye moieties which, when cleaved from the substrate during hydrolysis, provide fluorescent dyes having maximum absorptions above about 530 nm and maximum emissions at least about 580 nm at physiological pH. These substrates can be used in analytical determinations of hydrolytic substances including hydrolytic enzymes or biological cells containing such enzymes.

18 Claims, No Drawings

HYDROLYZABLE FLUORESCENT SUBSTRATES AND ANALYTICAL DETERMINATIONS USING SAME

CROSS-REFERENCE TO RELATED APPLICATIONS

Reference is made to the following copending and commonly assigned applications:

U.S. Ser. No. 824,757, filed on even date herewith by Babb et al and entitled BIOLOGICAL AND NALYTICAL USES IOF PHENALENONE AND BENZPHENALENONE COMPOUNDS, U.S. Ser. No. 824,755, filed on even date herewith by A. Wu and entitled USE OF POLYMERIC MORDANTS TO INCREASE THE INTENSITY OF RIGID FLUORESCENT DYES, and U.S. Ser. No. 824,752, filed on even date herewith by Sundberg et al and entitled HYDROLYZABLE FLUORESCENT SUBSTRATES FOR PHOSPHATASES AND ANALYTICAL USE THEREOF.

FIELD OF THE INVENTION

This invention relates to hydrolyzable fluorescent substrates and analytical compositions and elements containing same. It also relates to a method for the determination of hydrolytic analytes, e.g. hydrolytic enzymes. This invention is useful in the field of clinical chemistry.

BACKGROUND OF THE INVENTION

Chemical analysis of liquids, such as water, milk and biological fluids is often desirable or necessary for health maintenance and diagnostic treatment. Various compositions and elements to facilitate such analyses are known. Such materials generally comprise a reagent composition for determining the substance under analysis, identified herein as an "analyte". The analyte can be living cells, such as yeast cells, white blood cells or other living organisms, or a nonliving chemical substance. The reagent composition, upon interaction with the analyte, provides a detectable change (e.g. dye formation) which can be quantified in some manner.

The determination of specific hydrolytic enzymes in biological fluids can be useful for the diagnosis and treatment of certain diseases. It can also be useful for determining the presence of certain microorganisms because the metabolism of an organism is dependant upon the presence of a wide range of enzymes.

A number of analytical procedures have been developed whereby a substrate for an enzyme of interest is hydrolyzed to release a detectable moiety. These procedures use both colorimetric and fluorometric dyes. See, for example the assays described by Brown et al (J. Clin. Microbiology 21, p. 857, 1985) for pathogenic Nisseria spp., by Wasilauskas et al (J. Clin. Microbiology, 20, p. 1669, 1985) for Group A Streptococci, in the textbook edited by Norris (Methods of Microbiology, Vol. 9, Chapter 1, 1976) and by Kilian et al (Acta Path. Microbiol. Scand. B, 84, p. 245, 1976) for glycosidases.

Fluorometric assays are generally preferred because of generally greater sensitivity. However, known fluorometric assays are deficient in a number of ways. For example, E.P. application 122,148 (published Oct. 17, 1984) describes an assay for microorganisms using certain coumarin derivative as substrates which release dyes when the substrate is hydrolyzed. Although this assay is conducted at physiological pH for maximum biological activity, the pH is subsequently raised to 11 to obtain maximum fluorescence efficiency. Assays that require such a change in pH are not readily adaptable for highly automated analytical procedures.

U.S. Pat. No. 4,409,140 (issued Oct. 11, 1983 to Smith et al) describes an assay for proteolytic enzymes carried out at relatively lower pH, i.e. less than pH 8. The assay uses certain coumarin substrates which release a chromophore which fluoresces at 505 nm. At these relatively short wavelengths, however, spectral interferents (e.g. from hemoglobin and bilirubin) can be significant, severely limiting the sensitivity of the assay.

Other known assays require additional reagents, e.g. diazonium compounds, to give detectable moieties, as described in U.K. patent application No. 2,031,949 (published Apr. 30, 1980). Recently improved fluorescent umbelliferone derivatives have been described by Wolfbeis et al (Bull. Chem. Soc. Japan 58, p. 731, 1985) and used in an assay for acid phosphatase (Anal. Biochem. 143, p. 146, 1984). One of these dyes emits at 595 nm, but its absorption is at 505 nm where spectral interferents are a problem.

It is desirable to have fluorescent assays which are not subject to the problems associated with known assays, e.g. spectral interferents, and which can be readily used in automated analytical procedures.

SUMMARY OF THE INVENTION

The present invention overcomes the problems noted above with hydrolyzable compounds represented by the formula:

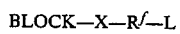

wherein BLOCK is a hydrolyzable group, X is —O—, —S— or —NR—, R is hydrogen, substituted or unsubstituted alkyl, substituted or unsubstituted cyclohexyl, substituted or unsubstituted phenyl or a substituted or unsubstituted heterocyclic group, R$^f$ is a substituted or unsubstituted phenalenone or benzphenalenone moiety provided that when released as —X—R$^f$—L, —X—R-$^f$—L exhibits maximum fluorescence emission at least about 580 nm and maximum absorption above about 530 nm at a pH of 9 or less, and L is hydrogen or a specific binding ligand.

An analytical composition of this invention comprises an aqueous solution buffered to a pH of 9 or less and containing the hydrolyzable compound described above.

Further, this invention provides an analytical element comprising an absorbent carrier material and containing the hydrolyzable compound described above.

Still further, a method for the determination of a hydrolytic analyte comprises the steps of:

A. under hydrolyzing conditions, contacting a sample of a liquid suspected of containing a hydrolytic analyte with the hydrolyzable compound described above, and B. determining the fluorescent moiety released from the compound by hydrolysis as a result of the presence of the analyte at a wavelength at least about 580 nm after excitation at a wavelength above about 530 nm.

The present invention provides novel substrates which release fluorescent dyes which are ionized at pH values less than 9 and thus exhibit maximum fluorescence at physiological pH. Advantageously, these dyes absorb and emit radiation away from spectral interferents commonly encountered in biological fluids. Further, the fluorescence emission spectra of the released dyes is shifted, i.e. it is different from that of the substrates themselves.

The assay of this invention which uses the substrates noted above is rapid and highly sensitive. It can be carried out at a relatively low pH, and the pH need not be changed as in known assays, making this invention adaptable to automated analytical procedures.

DETAILED DESCRIPTION OF THE INVENTION

The present invention can be used to determine qualitatively or quantitatively a hydrolytic analyte (living or nonliving). As used in this application the term "hydrolytic analyte" refers to a substance (chemical substance, enzyme or organism) which is capable of hydrolyzing the substrate of this invention by cleaving the BLOCK group from the remainder of the molecule at a pH of 9 or less. This invention is particularly useful for determining hydrolytic enzymes, such as esterases, amidases, proteases, and microorganisms containing these enzymes, such as Nissera spp., including those enzymes and microorganisms listed in WO patent application No. 80/02433 (published Nov. 13, 1980). The substrate can be designed with the appropriate BLOCK group and linkage to determine a particular analyte. For example, the invention can be used to identify *Enterobacter cloacae* and *Klebsiella pneumoniae* when BLOCK is derived from a monosaccharide moiety, L is hydrogen and X is oxy.

The substrates of this invention can be used in analytical determinations of various aqueous liquids, e.g. biological fluids, manufacturing processes, wastewater, food stuffs, etc. They can be used as labels or ligand analogs in specific binding assays as described in more detail below. The determinations can be made via a single reaction or a sequence of reactions which brings about hydrolysis of the substrate and release of the fluorescent dye.

The present invention is particularly useful for the determination of hydrolytic enzymes, cells or microorganisms in biological fluids, e.g. urine, cerebral spinal fluid, blood, lymph fluids, tissue homogenate, mucous, saliva, stool secretions, etc.

The substrates of this invention are represented by the formula:

BLOCK—X—R—L.

In this formula, BLOCK represents any suitable blocking group which can be cleaved from the remainder of the molecule by hydrolysis at a pH of 9 or less. Generally the blocking group is chosen based on the analyte specificity desired. Representative blocking groups include, for example, —CO—$R^1$, phosphono or thioxophosphono or a salt thereof, or a moiety derived from an amino acid, peptide or mono- or polysaccharide.

$R^1$ can be hydrogen, substituted or unsubstituted alkyl (preferably of 1 to 20 carbon atoms, e.g. methyl, ethyl, chloroethyl, isopropyl, benzyl, chlorobenzyl, etc.), substituted or unsubstituted alkenyl (preferably of 2 to 20 carbon atoms, e.g. ethenyl, 2-propenyl, 4-hexenyl, etc.), substituted or unsubstituted aryl (preferably of 6 to 12 carbon atoms, e.g. phenyl, methoxyphenyl, etc.), substituted or unsubstituted cycloalkyl (preferably of 5 to 12 carbon atoms, e.g. cyclopentyl, cyclohexyl, etc.), or a substituted or unsubstituted heterocyclic group (preferably of 6 to 12 carbon, sulfur, nitrogen and oxygen atoms, e.g. pyridyl, thienyl, etc.).

The X group of the formula above is oxy, thio, or imino (—NR—, wherein R is hydrogen or substituted or unsubstituted alkyl of 1 to 10 carbon atoms, e.g. methyl, ethyl, propyl, isopropyl, decyl, benzyl, etc., substituted or unsubstituted cyclohexyl, substituted or unsubstituted phenyl or a substituted or unsubstituted heterocyclic group as defined above, e.g. pyridyl, thienyl, etc.). Preferably, X is oxy or imino wherein R is hydrogen or lower substituted or unsubstituted alkyl of 1 to 3 carbon atoms.

$R^f$ is a moiety derived from a substituted or unsubstituted phenalenone or benzphenalenone fluorescent compound. When BLOCK is cleaved from the remainder of the molecule by hydrolysis, the resulting hydrolyzed moiety can preferably be detected at a pH of 9 or less. Most preferably, the hydrolyzed moieties can be detected at a pH of about 6 or less. Further, when excited at a wavelength above about 530, the hydrolyzed moiety exhibits maximum fluorescence at a wavelength of at least about 580 nm.

Useful phenalenone or benzphenalenone fluorescent moieties are selected from the group consisting of

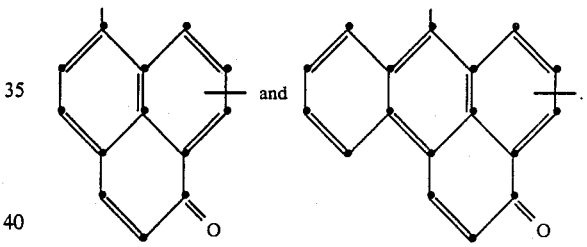

Representative compounds from which these moities are derived include:

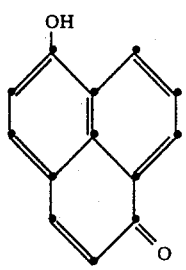

I.

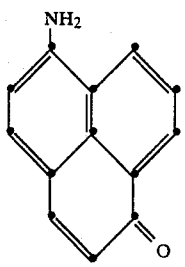

II.

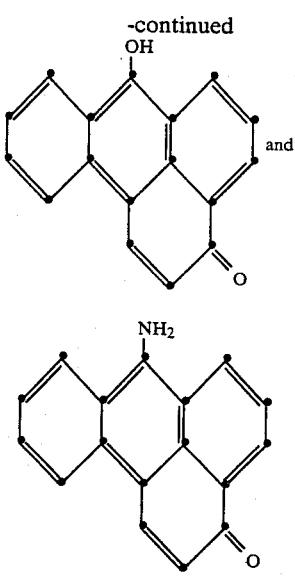

Compounds I and II are particularly useful in the practice of this invention.

These fluorescent moieties can have one or more other substituents which do not adversely affect their fluorescence or pKa value at one or more positions on one or more of the fused rings. Such substituents include substituted or unsubstituted alkyl (preferably of 1 to 12 carbon atoms, e.g. methyl, ethyl, benzyl, etc.), substituted or unsubstituted hydroxyalkyl (preferably of 1 to 12 carbon atoms, e.g. hydroxymethyl, 2-hydroxyethyl, etc.), substituted or unsubstituted alkoxycarbonyl (preferably of 2 to 12 carbon atoms, e.g. methoxycarbonyl, ethoxycarbonyl, etc.), halo (e.g. fluoro, chloro, bromo), cyano, carboxy, acyl, substituted or unsubstituted arylsulfonyl (preferably of 6 to 10 carbon atoms, e.g. phenylsulfonyl, tolylsulfonyl, etc.), substituted or unsubstituted alkylsulfonyl (preferably of 1 to 6 carbon atoms, e.g. methylsulfonyl, ethylsulfonyl, etc.), and other substituents known to one skilled in the art.

Fluorescent compound I identified above can be prepared by the method described by Cooke et al in *Australian J. Chem.*, 11, pp. 203-235 (1958). Fluorescent compounds II and IV can each be prepared by the method described by Solodar et al in *Zhurnal Organcheskoi Khimii* 16(5), pp. 1062-1064 (1980). Fluorescent compound III is prepared by the procedure described in U.S. Ser. No. 824,757 of Babb et al noted above.

Generally, the substrates of this invention are prepared by the following steps: (1) the preparation of the phenalenone or benzphenalenone dye and (2) reaction of the dye with an appropriate blocking reagent to form the blocked substrate. Representative preparations are provided in Examples 1, 3 and 5 below.

In the formula shown above, L is preferably hydrogen. However, L can also be a specific binding ligand so that the substrate can be used in a substrate-labeled fluorescent immunoassay as described for example in U.S. Pat. No. 4,279,992 (issued July 21, 1981 to Boguslaski et al). In such assays, the analyte to be determined is a ligand which will complex with a specific receptor. The assay is based on using a label that is a fluorogenic enzyme substrate. When the label is hydrolyzed by a specific enzyme, it yields a fluorescent product. In the present invention, the fluorescent product (phenalenone or benzphenalenone) advantageously has maximum absorption at a wavelength above about 530 nm and maximum emission at a wavelength at least about 580 nm. Binding of the labeled ligand by the receptor prevents the enzyme from hydrolyzing the substrate. Since a fluorescent product will not be produced by antibody-bound label, bound label can be distinguished from unbound label.

The assay can be used for the determination of any specific binding ligand, particularly haptens, such as drugs, and antibodies, antigens, hormones, polypeptides, etc. The substrates can also be used in what are known in the art as "sandwich" assays.

When L is a specific binding ligand, it is attached to R$^f$ by a covalent linking group. It will be recognized that there are many methods for covalently linking the ligand to R$^f$. The particular chemical character of the linking group will depend upon the nature of the respective available linking sites on the ligand and R$^f$. Selection of the linking group depends upon preservation of the ability of the ligand to participate in the specific binding reaction and the retention of desired pKa, absorption and emission properties. Generally, the linking group comprises a single or a double bond, or a chain containing between 1 and 10 carbon or heteroatoms in the chain. Particular examples of useful linking groups and methods of preparing —R$^f$—L are described in U.S. Pat. No. 4,279,992 noted above.

Depending upon their water solubilities, the substrates of this invention can be either dissolved directly in buffers or in a combination of buffer and water-miscible organic solvents, or solutions can be prepared containing a substrate, buffer, water-miscible organic solvent and surfactant.

When used for the determination of enzymes or organisms, the solution is buffered at 9 or less with one or more appropriate buffers. Useful buffers are readily determined by one skilled in the art and include phosphates, borates, and organic buffers as reported by Good et al in *Biochem.* 5, 467 (1966) and *Anal. Biochem.* 104, 300 (1980). Preferably the solution is buffered to a pH of 8 or less.

Surfactants which are useful in the practice of this invention include any surfactants which do not inhibit compound hydrolysis. Generally, for detection of living cells, the useful surfactants are nonionic surfactants, including, for example, alkylarylpolyethoxy alcohols (e.g. Triton X-100 and X-305 available from Rohm & Haas, Philadelphia, Pa., p-alkylarloxy polyglycidols (e.g. SURFACTANT 10G available from Olin Corp., Stamford, Conn., U.S.A.), TWEEN 80 (available from ICI Americas, Inc., Wilmington, Del., U.S.A.), and others known to one skilled in the art.

Useful water-miscible organic solvents include alcohols (e.g. methanol, ethanol, propanol, etc.), N,N-dimethylformamide, dimethyl sulfoxide, acetonitrile, hexamethylenephosphoramide and the like. The particular solvent to be used for a particular substrate can be readily determined by routine experimentation.

A solution can be prepared in the following general manner with the particular details of such a preparation illustrated in Example 3 below. The substrate is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of solution. This preparation is generally carried out at room temperature.

These solutions generally contain a buffer in an amount effective to maintain a physiological pH (9 or less). The concentration of buffer in the dispersion can vary widely, but is generally from about 0.01 to about 0.5 molar. Representative buffers are described above.

The determination of living cells, and particularly of bacterial cells, is often carried out in the presence of a nutrient for those cells although its presence is not essential. Any nutrient medium can be used which contains useful carbon, and optionally nitrogen, sources. Suitable nutrient medium having proper components and pH are well known in the art.

Some enzyme analytes require an inducer, i.e. a material or a combination of materials that promote the formation of the enzyme in the cell. The type of inducer or induction medium used is dependent upon the enzyme to be formed and determined. In some cases, both an inducer and a nutrient may be needed to promote formation. Another method of induction is to incubate the substrate in the presence of the nutrient for several minutes at appropriate temperatures prior to testing for the analyte.

The present invention is adaptable to either solution or dry assays. In a solution assay, a solution (or aqueous dispersion) containing a substrate can be prepared and contacted by mixing with a liquid test sample containing the living cells or hydrolytic analyte to be determined. Generally the substrate is mixed with the test sample in a suitable container (e.g. test tube, petri dish beaker, cuvette, test device, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the resulting fluorescent dye with suitable detection equipment at a wavelength greater than about 590 nm.

The solution assay can also be carried out by contacting a porous absorbent material, e.g. paper strip, containing the test sample with a dispersion of the substrate. The analyte in the test sample can migrate from the porous material into the dispersion and initiate the analytical reactions needed for determination.

In solution assays, the amount of substrate present is at least about 0.01, and preferably from about 10 to about 100, millimolar. Other reagents needed for the assay can be present in amounts readily determined by one skilled in the art.

Alternatively, the method of this invention can be practiced using a dry analytical element. Such an element can be a absorbent carrier material, i.e. a thin sheet or strip of self-supporting absorbent or bibulous material, such as filter paper or strips, which contains the hydrolyzable substrate or a dried residue of a solution or dispersion comprising same. Such elements are known in the art as test strips, diagnostic elements, dip sticks, diagnostic agents and the like.

When employed in dry analytical elements, the substrate can be incorporated into a suitable absorbent carrier material by imbibition or impregnation, or can be coated on a suitable absorbent carrier material. Alternatively, the substrate can be added to the element during an assay. Useful carrier materials are insoluble and maintain their structural integrity when exposed to water or physiological fluids such as urine or serum.

Useful carrier materials can be prepared from paper, porous particulate structures, cellulose, porous polymeric films, wood, glass fibers, woven and nonwoven fabrics (synthetic and nonsynthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

A dry assay can be practiced to particular advantage with an analytical element comprising a support having thereon at least one porous spreading zone as the absorbent carrier material. The substrate can be in the spreading zone or in a different zone (e.g. reagent zone, registration zone, hydrophilic zone, etc.). The spreading zone can be prepared from any suitable fibrous or nonfibrous material or mixtures of either or both.

The spreading zone can be prepared using fibrous materials or woven into a fabric, as described in U.S. Pat. No. 4,292,272 (issued Sept. 29, 1981 to Kitajima et al) or from polymeric compositions (e.g. blush polymers) or particulate materials, with or without binding adhesives, as described in U.S. Pat. Nos. 3,992,158 (issued Nov. 16, 1976 to Przybylowicz et al) 4,258,001 (issued Mar. 24, 1981 to Pierce et al) and 4,430,436 (issued Feb. 7, 1984 to Koyama et al) asnd Japanese Patent Publication No. 57(1982)-101760 (published June 24, 1982). It is desirable that the spreading zone be isotropically porous, meaning that the porosity is the same in each direction in the zone as created by interconnected spaces or pores.

The dry analytical element of this invention preferably comprise a suitable nonporous support carrying the absorbent carrier material. Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection (i.e. reflectance or transmission spectroscopy) and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, subbing zone, etc. The zones are generally in fluid contact with each other, meaning that fluids, reagents and reaction products can pass between superposed regions of adjacent zones. Preferably, the zones are separately coated superposed layers, although two or more zones can be located in a single layer. Besides the Przybylowicz et al and Pierce et al patents noted above, suitable element formats and components are described also, for example, in U.S. Pat. Nos. 4,042,335 (issued Aug. 16, 1977 to Clément) and 4,144,306 (noted above) and Reissue No. 30,267 (reissued May 6, 1980 to Bruschi).

In the elements of this invention, the amount of the substrate can be varied widely, but it is generally present in a coverage of at least about 0.001, and preferably from about 0.05 to about 1, g/m$^2$. Optional, but preferred reagents (e.g. nutrient, inducer, buffer, etc.) are generally present in the following coverages:

nutrient: generally at least about 0.05, and preferably from about 0.1 to about 2, g/m² (used only in living cell detection), buffer (pH≦9): generally at least about 0.1, and preferably from about 0.5 to about 2, g/m², and surfactant: generally at least about 0.1, and preferably from about 0.2 to about 5, g/m².

inducer: generally at least about $10^{-4}$ g/m².

One or more of the zones can contain a variety of other desirable, but optional, components, including activators, binders (generally hydrophilic), coupler solvents, etc. as is known in the art, as well as any reagent needed for assay of a particular hydrolytic analyte.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and physically contacting it with a sample (e.g. 1–200 μl) of the liquid to be tested so that the sample is mixed with the reagents in the element. Such contact can be accomplished in any suitable manner, e.g. dipping or immersing the element into the sample or, preferably, by spotting the element by hand or machine with one or more drops of the sample with a suitable dispensing means. This contact causes the liquid sample to be mixed within the element with the substrate and any other reagents therein.

After sample application, the element is exposed to any conditioning, such as incubation, heating or the like, that may be desirable to quicken or otherwise facilitate obtaining a test result.

Generally, the assay (solution or dry) is carried out under conditions that promote hydrolysis of the substrate by the hydrolytic enzyme. Such hydrolyzing conditions include conditions of pH and temperature which are conducive to hydrolysis. Generally, the pH will vary from one analyte to another, but for biological analytes will be less than 9, and preferably less than 8. The temperature is not critical but is generally up to about 50° C.

Detection of an analyte or living cell is achieved when the substrate is hydrolyzed releasing a fluorescent moiety which can be detected in a suitable manner at greater than about 580 nm. It is not necessary, however, for the determination to be made at the wavelength of maximum fluorescence. Determination can be either a rate determination or an endpoint determination. The time of reaction can vary from analyte to analyte and can be readily chosen by a skilled clinical chemist.

In the examples which follow illustrating the practice of the invention, the materials used were obtained as follows:

Triton X-100 surfactant from Rohm and Haas (Philadelphia, Pa., U.S.A.), the bacterial microorganisms from American Type Culture Collection (ATCC in Rockville, Md., U.S.A.), Dynatech Micofluor Reader from Dynatech Labs (Alexandria, Va., U.S.A.), Millititer HA 96 well titration plate from Millipore Corp. (Bedford, Mass., U.S.A.), and the remainder were obtained from Eastman Kodak Co. (Rochester, N.Y., U.S.A.) or prepared using known starting materials and procedures.

As used in the context of this disclosure and the claims, I.U. represents the International Unit for enzyme activity defined as one I.U. being the amount of enzyme activity required to catalyze the conversion of 1 μmole of substrate per minute under standard pH and temperature conditions for the enzyme.

In the following examples, the identity and purity of intermediates compounds were determined by infrared (IR) spectra as measured in a commercially available Perkin-Elmer 710B spectrophotometer [sharp(s) or broad(b) bands yielding structural information are reported in reciprocal centimeters (cm$^{-1}$)] or by nuclear magnetic resonance (NMR) spectra measured with an IBM-WP 2705Y (270 Mz) or Varian EM390, for proton NMR and FX 270 JEOL (67.8 Mz) for carbon NMR [chemical shifts reported in δ values in ppm to tetramethylsilane] or by mass spectral analysis measured in a Varian MAT 731. The identity and purity of final products were determined by IR, NMR spectroscopy or mass spectral analysis or elemental analysis.

EXAMPLE 1

Preparation of Substrate Having a Monosaccharide Blocking Group

The following compound was prepared:

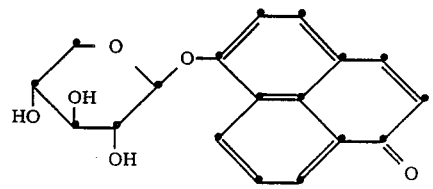

Preparation of 1,2,3,4-Tetracetyl-D-xylopyranose

This material was prepared by the method described by M. L. Wolfrom and A. Thompson in *Methods in Carbohydrate Chemistry*, II, p. 211, edited by R. L. Whistler and M. L. Wolfrom, New York, Academic Press, 1963. From 50 g of D-xylose, there was obtained 88 g of Intermediate A.

Preparation of 1-Bromo-2,3,4-triacetyl-β-D-xylopyranose

This material was prepared by the method described by K. Bock, C. Pederson, and P. Rasmussen, *Acta Chem. Scand.*, B29 (1975), 389–393. From 2.5 g of 1,2,3,4-tetraacetyl-D-xylopyranose, there was obtained 1 g of Intermediate B, mp. 97°–98° C.

Preparation of 1-(6-Oxyphenalenone)-2,3,4-triacetyl-β-D-xylopyranose

To a mixture of 6-hydroxyphenalenone (4.8 g 29 mmole) and silver carbonate (7.9 g, 29 mmole, D. R. Lineback in *Methods in Carbohydrate Chemistry*, II, p. 341 (edited by R. L. Whistler and M. L. Wolfrom, New York, Academic Press, 1963) in pyridine (105 ml) was added Intermediate B (6 g, 17 mmole). The mixture was stirred for 18 hours at room temperature in the dark, at which time it was poured into 2 liters of a 10% HCl/ice water solution. The precipitated material was filtered, washed with ice water, and air dried. The crude Intermediate C (17 g) was chromatographed on neutral alumina (eluent: 60/40 dichloromethane/ethyl acetate). There was obtained 3.8 g of product.

Preparation of 1-(6-Oxyphenalenone)-β-D-xylopyranose

To a suspension of 1-(6-oxyphenalenone)-2,3,4-triacetyl-β-D-xylopyranoside (3.8 g, 8.4 mmole) in 25 ml anhydrous methanol was added sodium methoxide (8.4 ml, 1 molar solution). The mixture was stirred for 45 minutes, at which time the yellow precipitated solid was filtered, rinsed with methanol, and dried. The yield of product shown above was quantitative. The material decomposes slowly, with final decomposition at about 215° C.

Analysis: calculated for $C_{18}H_{16}O_6$: C, 65.8, H, 4.9, O, 29.2. Found: C, 64.8, H, 5.0, O, 29.3.

EXAMPLE 2

Detection of *Enterobacter cloacae* and *Klebsiella pneumoniae*

Cells were prepared as follows. A β-D-xylosidase induction medium was prepared by adding the following materials in order to 350 μl of 0.1 molar sodium, potassium phosphate buffer (pH 7.0), 25 μl 5% yeast extract, 50 μl of 4% $(NH_4)_2HPO_4$ and 1% KCl, 50 μl 0.0075% $MnSO_4.H_2O$ and 0.01% $FeSO_4.7H_2O$. This mixture was autoclaved for 30 minutes, then cooled. Just before incubation, 25 μl of 20% xylose solution and 2% $MgSO_4.7H_2O$, which had been filter sterilized or autoclaved separately, were added. *Klebsiella pneumoniae* (ATCC 13882) and *Enterobacter cloacae* (ATCC 23355) were both grown in this medium for 18 hours at 37° C. Ten milliliters of cells were harvested by centrifugation, washed, and resuspended in 0.1 molar potassium phosphate buffer (pH 7.0). The cell concentration was adjusted to approximately $5 \times 10^8$ cells/ml (optical density 0.800 at 620 nm).

In two milliliters HA 96 well titration plates were placed 200 μl of the cell suspension. To plate 1 was added 100 μl of the substrate solution of Example 1 without surfactant (10 μg/μl N,N-dimethylformamide in 9 μl potassium phosphate buffer), to plate 2 was added the substrate solution with surfactant (10 μg/μl N,N-dimethylformamide and 200 μl TRITON X-100 surfactant in 9 μl potassium phosphate buffer).

After the substrate was added, an initial reading was taken, the plates were kept at 37° C., and additional readings were taken after 5, 10, 15, 30, and 60 minutes. The average of three replicates was used. A commercially available Dynatech Microfluor Reader, modified with an excitation filter at 540 nm, an emission filter at 620 nm, a 200-watt tungsten lamp and a heating element, was used to measure fluorescence. The Controls did not contain any cells.

The results, shown in Table II below, indicate that both substrate solutions can be used to detect the microorganisms as quickly as 15 minutes.

TABLE II

| Minutes | Relative Fluorescence | | |
|---|---|---|---|
| | Control | Enterobacter | Klebsiella |
| Millititer Plate 1 | | | |
| 0 | 519 | 525 | 500 |
| 5 | 571 | 684 | 585 |
| 10 | 611 | 925 | 698 |
| 15 | 606 | 1150 | 752 |

TABLE II-continued

| Minutes | Relative Fluorescence | | |
|---|---|---|---|
| | Control | Enterobacter | Klebsiella |
| 30 | 672 | 2245 | 1205 |
| 60 | 688 | 2717 | 1686 |
| Millititer Plate 2 | | | |
| 0 | 548 | 586 | 557 |
| 5 | 586 | 902 | 635 |
| 10 | 597 | 1341 | 741 |
| 15 | 615 | 1795 | 869 |
| 30 | 611 | 2626 | 1232 |
| 60 | 618 | 3003 | 1976 |

EXAMPLE 3

Solution Determination of an Esterase Enzyme

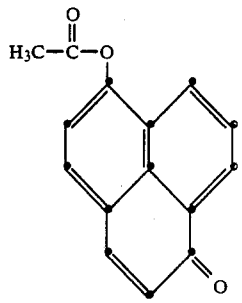

The substrate shown above was prepared by heating 3 g of 6-hydroxyphenalenone in 20 ml of acetic anhydride with stirring until solution was obtained. The excess acetic anhydride was removed under reduced pressure. The residue was dissolved in warm methanol, cooled and treated with water until the product began to precipitate. The solid was collected by filtration and dried to give 2.6 g of product. Mass spectral analysis confirmed the structure.

A buffered solution of the substrate was prepared as follows. The substrate in N,N-dimethylformamide (16 mg/ml solvent) was added to 500 μl TRITON X-100 surfactant, and the resulting solution was added slowly to 25 ml potassium phosphate buffer (0.05 molar, pH 7.5) with stirring.

Three milliliters of the buffered solution containing the substrate was placed in each of two quartz cells. To one cell was added 10 μl of a solution containing diacetinase (0.218 I.U. diacetinase per μl of potassium phosphate buffer, pH 7.5). The second cell was the Control. The relative fluorescence of each cell solution was measured at various times with a commercially available Perkin-Elmer fluorometer (excitation, 540 nm, maximum emission, 620 nm) at pH 7.5 and 25° C. The results, shown in Table I, indicate a rapid generation of fluorescence in the cell containing the esterase enzyme, diacetinase. The Control showed only minimal increase in fluorescence.

TABLE I

| Time (Minutes) | Relative Fluorescence | |
|---|---|---|
| | Control Cell | Test Cell |
| 0 | 123 | 134 |
| 0.5 | 124 | 142 |
| 1.0 | 124 | 150 |
| 3.0 | 125 | 161 |
| 5.0 | 127 | 175 |
| 7.0 | 129 | 202 |
| 10.0 | 130 | 238 |

TABLE I-continued

| Time (Minutes) | Relative Fluorescence | |
|---|---|---|
| | Control Cell | Test Cell |
| 15.0 | 134 | 266 |

EXAMPLE 4

The Determination of Esterase Activity in White Blood Cells

This example demonstrates that an esterase substrate can be used to assay for the presence of white blood cells.

Leucocyte-rich layers (buffy coats) were purified from blood of healthy adult donors (taken in ACD tubes*) by adding 1.5 ml of Dextran T70 (6% in balanced salt solution), purchased from Pharmacia Fine Chemical (Piscataway, N.J., U.S.A.), to a 10 ml tube of blood. The tubes were allowed to set for one hour, then the plasma layer was transferred to sterile 15 ml centrifuge tubes, and the tubes were filled up to 7.5 ml with PBS solution (8.5 g sodium chloride in 0.05 molar potassium phosphate buffer, pH 7.5). The tubes were centrifuged at 1000 RPM for 10 minutes. The resulting cell pellet was resuspended in 10 ml lysing solution [0.83 g ammonium chloride, 0.1 g sodium bicarbonate and 0.003 g (ethylenedinitrilo)tetraacetic acid disodium salt in 100 ml of water, pH 7.2], and the tubes were allowed to set until the solution cleared. The tubes were again centrifuged, and the pellet was washed and resuspended in PBS. Cells were counted and adjusted to about $10^6$ cells/ml.

Three milliliters of various concentrations of white blood cells in potassium phosphate buffer (0.05 molar, pH 7.5) were mixed with 10 μl of the substrate of Example 3 (10.77 mg/μl methanol), and the relative fluorescence was measured at an excitation wavelength of 540 nm and a maximum emission wavelength of 620 nm. Results are shown in Table III below.

TABLE III

| Sample | Cell Conc/μl | Relative Fluorescence | | | |
|---|---|---|---|---|---|
| | | 0 Min | 10 Min | 15 Min | 30 Min |
| 1 (Control) | 0 | 15.9 | 27.0 | 31.9 | 45.8 |
| 2 | $4.92 \times 10^3$ | 28.2 | 37.1 | 42.6 | 60.4 |
| 3 | $4.92 \times 10^4$ | 23.2 | 41.7 | 48.8 | 70.3 |
| 4 | $4.92 \times 10^5$ | 25.6 | 69.0 | 85.0 | 124.0 |

*ACD (acid, citrate, dextrose B-D4606) prefilled blood collection tubes purchased from VWR Scientific (Rochester, New York, U.S.A.).

EXAMPLE 5

The Determination of Various Hydrolytic Enzymes

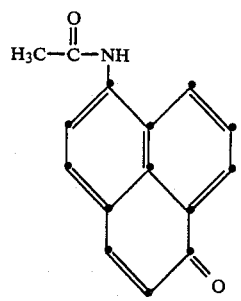

This example demonstrates that the substrate illustrated above can be used to assay for various hydrolytic enzymes.

The substrate illustrated above was prepared by adding 1 g of sodium acetate and 2 ml of acetic anhydride to a solution of 0.6 g of 6-aminophenalenone in 10 ml of acetic anhydride, and heating this mixture until solution was obtained. Thin layer chromatography (silica, 3:2 ethyl acetate, toluene) did not show any starting material. The solution was added to water (100 ml), and the mixture was extracted several times with ethyl acetate. The combined extracts were dried and concentrated under reduced pressure to give 0.3 g of product. Mass spectral analysis confirmed the structure.

Test solutions were prepared with the following: 50 μl of substrate (1 mg/μl methanol), 3 μl of 0.05 molar potassium phosphate buffer at the indicated pH (near the optimum for each enzyme) and 10 μl of enzyme. Enzymes to be determined included carboxylesterase, Type I (pH 7.8) and Type II (pH 6.0), aminoacylase, Grade I (pH 7.0), and trypsin, Type I and III (pH 7.8). Sample preparations and testing were done in an area protected from light. The enzyme solutions were kept at 0° C. prior to use, and assays were run at 25° C. with fluorescence measured at an excitation of 540 nm and an emission of 595 nm. The results are shown in Table IV below.

TABLE IV

| Enzyme[b] | Final Enzyme Activity (I.U.) | Relative Fluorescence[a] | | | |
|---|---|---|---|---|---|
| | | 0 Min | 10 Min | 15 Min | 30 Min |
| Carboxy-lesterase (Type I) | 9.6 | 2.7 | 3.6 | 4.1 | 4.4 |
| | 96 | 3.0 | 6.1 | 7.9 | 12.5 |
| Carboxy-lesterase (Type II) | 15 | 2.0 | 5.4 | 8.0 | 15.8 |
| Aminoacylase (Grade I) | 3,000 | 1.5 | 2.0 | 2.1 | 2.3 |
| Trypsin (Type I) | 5,000 | 0 | 0.5 | 0.6 | 0.8 |
| | 50,000 | 0 | 0.7 | 0.9 | 1.5 |
| Trypsin (Type III) | 6,000 | 2.7 | 2.8 | 3.0 | 3.6 |
| | 60,000 | 2.2 | 3.5 | 3.4 | 4.3 |

[a]Minus control with no enzyme.
[b]Enzymes were obtained from Sigma Chemical Company (St. Louis, Missouri), and enzyme types are those of the supplier.

EXAMPLE 6

Determination of Esterase Activity in a Dry Analytical Element

This example illustrates the use of the substrate shown in Example 3 in a dry analytical element for the determination of an esterase.

A strip of Whatman No. 2 filter paper (VWR Scientific Co., Rochester, N.Y., U.S.A.) was immersed in a solution of the substrate in methanol (3 mg in 0.5 ml). The paper was then allowed to dry at 37° C. for two hours.

A carboxy esterase (Esterase, Type II, 100 I.U./mg protein from Sigma Chemical Co., St. Louis, Mo., U.S.A.) was dissolved in 0.05 molar potassium phosphate buffer (pH 7.5), 10 μg/ml of buffer. A sample (10 μl) of this solution was applied to the filter paper and the sample came into contact with the substrate therein. A Control solution containing only buffer was applied to a separate area of the element. After 1 minute incubation at 37° C., the element was visually examined. The area of the element contacted with esterase enzyme became a bright orange indicating the presence of the enzyme, while the area contacted with the Control solution exhibited no color change.

The invention has been described in detail with particular reference to preferred embodiments thereof, but it will be understood that variations and modifications can be effected within the spirit and scope of the invention.

We claim:

1. A hydrolyzable compound represented by the formula:

BLOCK—X—R$^f$—L 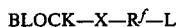

wherein BLOCK is a hydrolyzable group selected from the group consisting of:
—COR$^1$; a monovalent moiety derived by removal of a hydroxy group from a carboxy group of an amino acid or peptide; or a monovalent moiety derived by removal of a hydroxy group from a mono- or polysaccharide, R$^1$ is hydrogen, alkyl, alkenyl, aryl, cycloalkyl or a heterocyclic group, X is —O—, —S— or —NR— and is attached to BLOCK at the open valence on BLOCK wherein R is hydrogen, alkyl, cycloalkyl, phenyl or a heterocyclic group, R$^f$ is a phenalenone or benzphenalenone fluorescent moiety selected from the group consisting essentially of

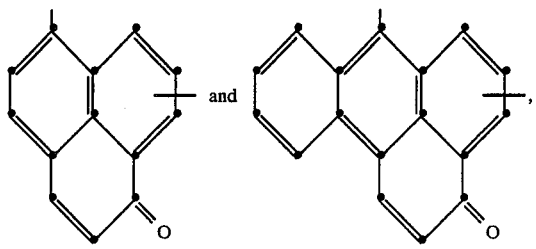

provided that when released as —X—R$^f$—L, —X—R$^f$—L exhibits maximum fluorescent emission at least about 580 nm at a pH of 9 or less, and L is hydrogen or a specific binding ligand.

2. The compound of claim 1 wherein BLOCK is —CO—R$^1$ wherein R$^1$ is hydrogen or alkyl.

3. The compound of claim 1 wherein L is hydrogen.

4. The compound of claim 1 wherein L is a specific binding ligand.

5. The compound of claim 1 wherein X is —O— or —NR—.

6. An analytical composition comprising an solution buffered to a pH of 9 or less and containing a hydrolyzable compound represented by the formula:

BLOCK—X—R$^f$—L 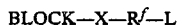

wherein BLOCK is a hydrolyzable group selected from the group consisting of:
—COR$^1$; a monovalent moiety derived by removal of a hydroxy group from a carboxy group of an amino acid or peptide: or a monovalent moiety derived by removal of a hydroxy group from a mono- or polysaccharide, R$^1$ is hydrogen, alkyl, alkenyl, aryl, cycloalkyl or a heterocyclic group, X is —O—, —S— or —NR— and is attached to BLOCK at the open valence on BLOCK, wherein R is hydrogen, alkyl, cycloalkyl, phenyl or a heterocyclic group, R$^f$ is a phenalenone or benzphenalenone fluorescent moiety selected from the group consisting essentially of

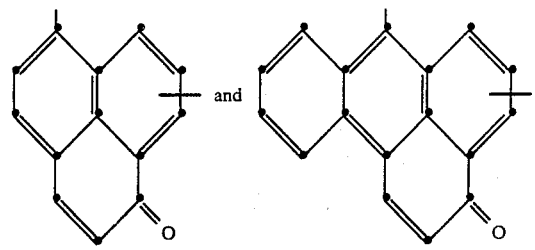

provided that when released as —X—R$^f$—L, —X—R$^f$—L exhibits maximum fluorescent emission at least about 580 nm and maximum absorption above about 540 nm at a pH of 9 or less, and L is hydrogen or a specific binding ligand.

7. The composition of claim 6 further comprising a water-miscible solvent and a surfactant.

8. The composition of claim 6 wherein BLOCK is —CO—R$^1$ wherein R$^1$ is independently hydrogen or alkyl, L is hydrogen and X is —O— or —NR—.

9. An analytical element comprising an absorbent carrier material and containing a hydrolyzable compound represented by the formula:

BLOCK—X—R$^f$—L 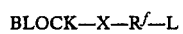

wherein BLOCK is a hydrolyzable group selected from the group consisting of:
—COR$^1$; a monovalent moiety derived by removal of a hydroxy group from a carboxy group of an amino acid or peptide; or a monovalent moiety derived by removal of a hydroxy group from a mono- or polysaccharide, R$^1$ is hydrogen, alkyl, alkenyl, aryl, cycloalkyl or a heterocyclic group, X is —O—, —S— or —NR— and is attached to BLOCK at the open valence on BLOCK, wherein R is hydrogen, alkyl, cycloalkyl, phenyl or a heterocyclic group, R$^f$ is a phenalenone or benzphenalenone fluorescent moiety selected from the group consisting essentially of

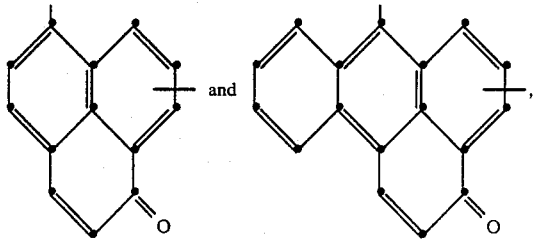

provided that when released as —X—R$^f$—L, —X—R$^f$—L exhibits maximum fluorescent emission at least about 580 nm and maximum absorption above about 530 nm at a pH of 9 or less, and L is hydrogen or a specific binding ligand.

10. The element of claim 9 further containing a buffer which maintains the pH at 9 or less during an assay.

11. The element of claim 9 comprising a nonporous support having therein a porous spreading zone as said absorbent carrier material.

12. The element of claim 9 wherein BLOCK is —CO—R¹ wherein R¹ is hydrogen or alkyl, L is hydrogen, and X is —O— or —NR—.

13. A method for the determination of a hydrolytic analyte comprising the steps of:
A. under hydrolyzing conditions, contacting a sample of a liquid suspected of containing a hydrolytic analyte with a hydrolyzable compound represented by the formula:

BLOCK—X—Rᶠ—L wherein BLOCK is a hydrolyzable group selected from the group consisting of:
—COR¹; a monovalent moiety derived by removal of a hydroxy group from a carboxy group of an amino acid or peptide; or a monovalent moiety derived by removal of a hydroxy group from a mono- or polysaccharide, R¹ is hydrogen, alkyl, alkenyl, aryl, cycloalkyl or a heterocyclic group, X is —O—, —S— or —NR— and is attached to BLOCK at the open valence on BLOCK, wherein R is hydrogen, alkyl, cycloalkyl, phenyl or a heterocyclic group, Rᶠ is a phenalenone or benzphenalenone fluorescent moiety selected from the group consisting essentially of

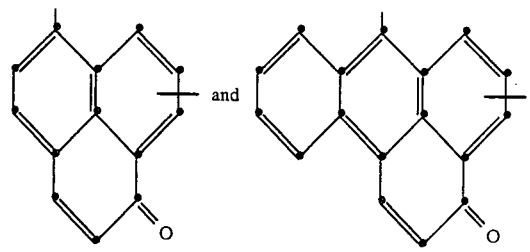

provided that when released as —X—Rᶠ—L, —X—Rᶠ—L exhibits maximum fluorescent emission at least about 580 nm and maximum absorption above about 530 nm at a pH of 9 or less, and L is hydrogen or a specific binding ligand, and B. determining the fluorescent moiety released from said compound by hydrolysis as a result of the presence of said hydrolytic analyte at a wavelength at least about 580 nm after excitation at a wavelength above about 530 nm.

14. The method of claim 13 carried out at a pH of 8 or less.

15. The method of claim 13 for the determination of a hydrolytic enzyme.

16. The method of claim 13 which is a competitive binding assay.

17. The method of claim 13 wherein BLOCK is —CO—R¹ wherein R¹ is hydrogen or alkyl, L is hydrogen, and X is —O— or —NR—.

18. The method of claim 13 for the determination of *Klebsiella pneumoniae* or *Enterobacter cloacae* wherein BLOCK is derived from a monosaccharide.

* * * * *